(12) United States Patent
Ahmed

(10) Patent No.: US 8,371,854 B2
(45) Date of Patent: Feb. 12, 2013

(54) METHOD FOR IN-SITU SIMULTANEOUS SHAPING OF ADJACENT MATRIX BANDS AND TOOLS

(76) Inventor: Adnan Ahmed, Perrysburg, OH (US)

( * ) Notice: Subject to any disclaimer, the term of this patent is extended or adjusted under 35 U.S.C. 154(b) by 0 days.

(21) Appl. No.: 12/930,560

(22) Filed: Jan. 11, 2011

(65) Prior Publication Data

US 2011/0171597 A1  Jul. 14, 2011

Related U.S. Application Data

(60) Provisional application No. 61/335,872, filed on Jan. 13, 2010.

(51) Int. Cl.
A61C 5/04 (2006.01)
(52) U.S. Cl. ........................................ 433/226
(58) Field of Classification Search .................. 433/141, 433/147–148, 156–160, 215, 226
See application file for complete search history.

(56) References Cited

U.S. PATENT DOCUMENTS

| | | | |
|---|---|---|---|
| 4,696,646 A | 9/1987 | Maitland | |
| 4,726,770 A | 2/1988 | Kurer | |
| 4,747,777 A | 5/1988 | Ward | |
| 4,836,781 A | 6/1989 | Meinershagen | |
| 5,098,300 A * | 3/1992 | Zaki | 433/229 |
| 5,318,446 A | 6/1994 | Slone | |
| 5,622,496 A * | 4/1997 | Champagne | 433/39 |
| 5,626,476 A * | 5/1997 | Champagne | 433/226 |
| 5,788,499 A | 8/1998 | Hoffman | |
| 5,947,731 A | 9/1999 | Fell | |
| 5,993,210 A * | 11/1999 | Godfrey | 433/159 |
| 6,186,786 B1 | 2/2001 | Trushkowsky | |
| 6,206,697 B1 | 3/2001 | Hugo | |
| 6,280,187 B1 | 8/2001 | Slone | |
| 6,345,983 B1 | 2/2002 | Godfrey | |
| 6,482,005 B1 | 11/2002 | Summer et al. | |
| 6,589,053 B2 | 7/2003 | Bills | |
| 6,652,277 B1 | 11/2003 | Godfrey | |
| 6,712,608 B2 | 3/2004 | Bills | |
| 6,860,737 B2 | 3/2005 | Ulso | |
| 7,037,109 B1 | 5/2006 | Viscomi et al. | |
| 7,108,509 B2 | 9/2006 | Heesen | |
| 7,165,970 B2 | 1/2007 | Anderson | |
| 7,381,055 B2 | 6/2008 | Jabri | |
| 2004/0142303 A1 | 7/2004 | Dryer | |
| 2005/0118554 A1 | 6/2005 | Kilcher et al. | |
| 2005/0255428 A1 | 11/2005 | Coopersmith | |
| 2006/0078845 A1 | 4/2006 | Heesen | |
| 2007/0087310 A1 | 4/2007 | Giusti | |
| 2008/0176179 A1 | 7/2008 | Coffee | |

* cited by examiner

Primary Examiner — Cris L Rodriguez
Assistant Examiner — Hao D Mai
(74) Attorney, Agent, or Firm — David C. Purdue

(57) ABSTRACT

A dental instrument with arms pivotally connected for scissors pivot action between closed and open positions is disclosed. A pair of tines extends from distal ends of the arms and at least one shaping surface on one of said tines is supported so that it is operable to shape an interior surface of one of two matrix bands positioned around adjacent teeth. In use, each tine is positioned inside of adjacent matrix bands positioned around adjacent teeth. As the arms are pivoted towards the closed position, the shaping surface is moved towards the tine on which it is not supported and a clamping force is applied by the tines causing the shaping surface to shape at least one of the matrix bands.

9 Claims, 7 Drawing Sheets

METHOD FOR IN-SITU SIMULTANEOUS SHAPING OF ADJACENT MATRIX BANDS AND TOOLS

BACKGROUND OF THE INVENTION

1. Field of the Invention

The present invention is a method for simultaneously shaping and positioning adjacent portions of two matrix bands surrounding adjacent teeth, and dental instrument especially suited for use in carrying out the method. The method and tool facilitate preparation for the concurrent placement of filling material in the bands to restore both teeth.

2. Description of the Prior Art

Matrix bands are made of malleable material such as metal and they are positioned around teeth after the teeth have been excavated to remove decayed material, to provide a solid foundation for filling material. Matrix bands contain filling material, such as resin filling material, and form it to and maintain it in a desired shape while it hardens or is hardened or cured.

The prior art discloses myriad dental instruments specifically designed to shape one or two portions of a single matrix band positioned around a single tooth. Examples are described and disclosed in U.S. Pat. Nos. 6,345,983 and 6,652,277. The instruments disclosed in these patents comprise tines supported at the end of two handle arms pivotally connected to each other so the tines spread apart as the handles are squeezed. The tines are manipulated so that outwardly facing shaping surfaces on each tine engage and shape portions of the matrix band and, specifically, the portions where the matrix banded tooth will contact adjacent teeth.

When decay strikes two adjacent teeth, as often happens, the prior art dental instruments described above virtually dictate that a dentist will have to repair those teeth one at a time. Due to the number of steps involved in filling a cavity, especially the curing or hardening of the filling material, this is not an efficient approach to repairing and filling two adjacent teeth. If both of the two adjacent affected teeth could be banded and the teeth filled with filling material, then the filling material in two teeth could be cured or hardened in a single step rather than in two separate steps. This would save considerable time, but the prior art dental instruments are wholly unsuited to shaping and positioning the matrix bands surrounding two adjacent teeth.

SUMMARY OF THE INVENTION

The instant invention is a method for simultaneously shaping adjacent portions of two matrix bands positioned around adjacent teeth, and a tool for use in that method. The tool is especially suited to simultaneously shape adjacent portions of two matrix bands, in-situ, so that the shaped bands can be filled concurrently with filling material and the material can harden or be hardened simultaneously in adjacent teeth.

Accordingly, it is an object of the invention to provide an improved method for shaping matrix bands.

It is another object of the invention to provide an improved dental instrument capable of simultaneously shaping adjacent portions of two matrix bands surrounding two adjacent teeth.

It is a further object of the invention to bring a new efficiency to the filling of cavities that result when decay spans two adjacent teeth, as it so often does.

It is yet another object of the invention to provide a dental instrument that simultaneously shapes adjacent portions of matrix bands surrounding two adjacent teeth to facilitate the concurrent filling of cavities in those teeth.

These and other objects and advantages will be apparent to one skilled in the dental arts from the description herein, reference being made to the attached drawing figures.

BRIEF DESCRIPTION OF THE DRAWING FIGURES

FIG. 1A is a top view of the instrument shown in FIG. 1.

DETAILED DESCRIPTION OF THE INVENTION

Figure 1:
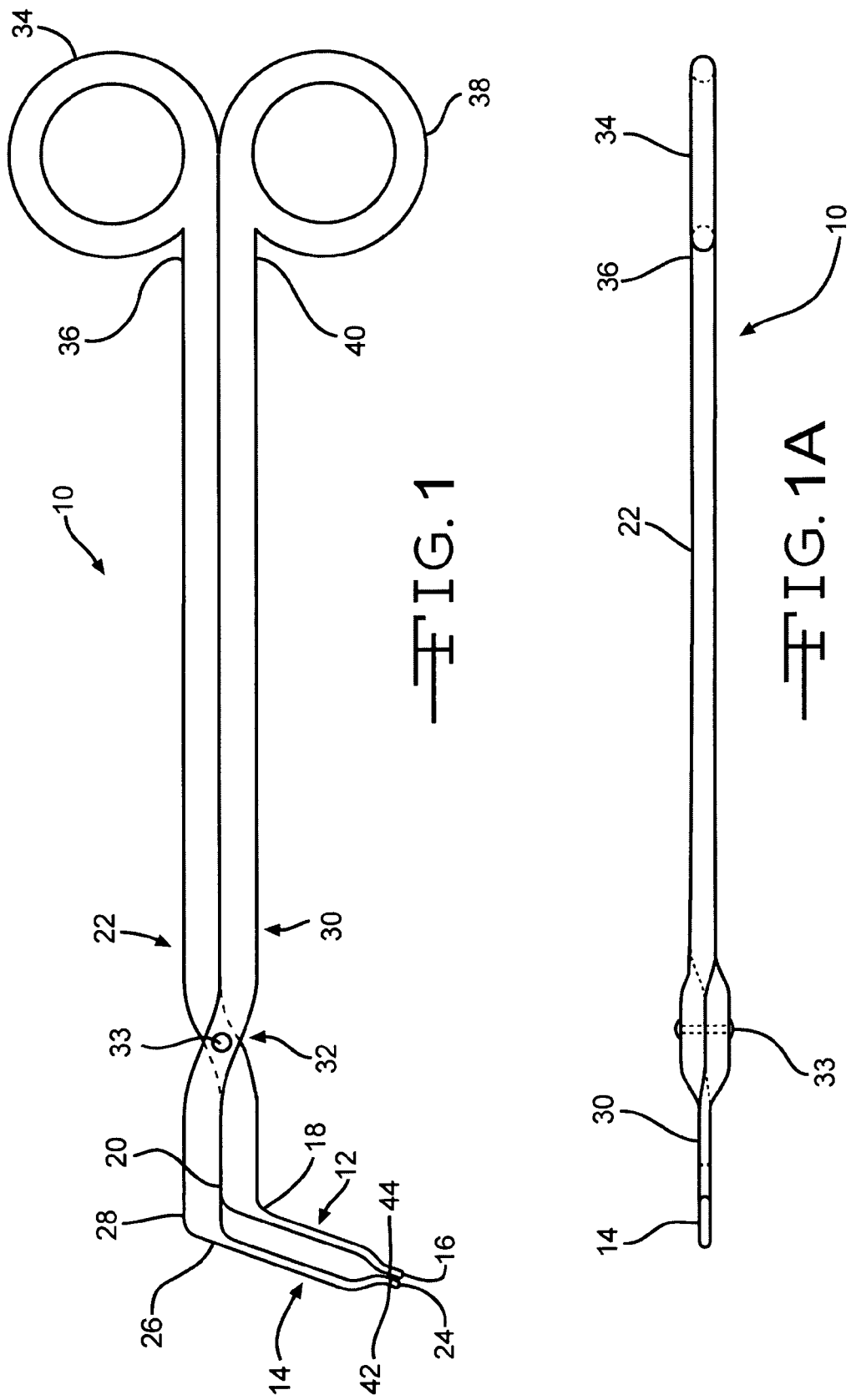
FIG. 1 is a side view of a dental instrument according to one embodiment of the invention.
Figure 11:
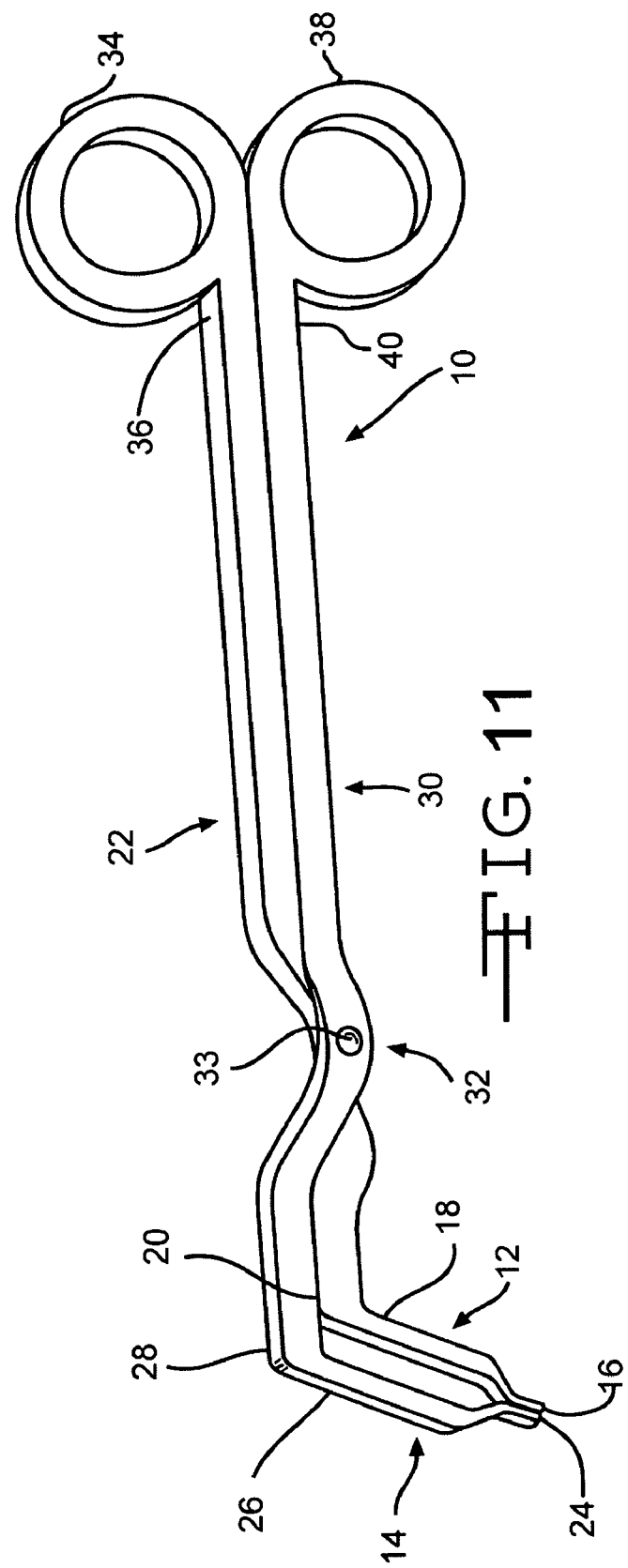
FIG. 11 is a perspective view of the dental tool shown in FIGS. 1, 1A, 3 through 5 and 8.

Referring now in more detail to the drawing figures, and especially FIGS. 1, 1A and 11, a dental instrument according to one embodiment of the invention is indicated generally at 10. The dental instrument comprises a first tine 12 and a second tine 14. The first tine 12 has a distal end 16 and a proximal end 18 which is supported by and depends from a first end 20 of a first arm 22. The second tine 14 has a distal end 24 and a proximal end 26 which is supported by and depends from a first end 28 of a second arm 30. The first arm 22 and the second arm 30 are pivotally connected at 32. A finger ring 34 is mounted on a second end 36 of the first arm 22. A finger ring 38 is mounted on a second end 40 of the second arm 30. The finger rings 34 and 38 can be manipulated towards and away from each other. When the finger rings 34 and 38 are manipulated towards each other, to the position shown in FIGS. 1 and 11, the distal ends 16 and 24 of the tines 12 and 14 are next to each other, as shown in these Figs. The distal ends 16 and 24 of the tines 12 and 14 can be separated by causing the finger rings 34 and 38 to move away from each other. This is a known scissors action and will not be described further.

As shown in FIG. 1A, the arms 22 and 30 are co-planar except in the vicinity of the pivotal connection 32, where the arms 22 and 30 cross. This construction minimizes the footprint of the instrument 10 making it better adapted for use in the close quarters of a human mouth. A pivot pin 33 extends through aligned openings in the arms 22 and 30 to make the pivot connection 32. The pivot connection 32 is positioned between the ends of the arms 22 and 30, but closer to the first ends 20 and 28 of the arms 22 and 30. The pivot connection 32 may be one that permits the easy disassembly of the arms 22 and 30. This type of pivot connection is known in some scissors where, when the arms are pivoted beyond the cutting range, at least one key on the head of the pivot pin aligns with a corresponding keyway or keyways in one of the arms so that one arm may removed from the pivot pin and the other arm. The pivot connection 32 permits pivotal movement between the arms 22 and 30 from a first, closed position, shown in FIGS. 1 and 11, where the second ends 36 and 40 of the arms 22 and 30 are adjacent to each other, and a second position where the second ends 36 and 40 of the arms 22 and 30 are spaced apart. The instrument 10 has a stop to prevent the arms from pivoting past the first position and it is the arms 22 and 30, themselves. When the arms 22 and 30 are in the first position, portions of the arms 22 and 30 abut, as can be seen in FIG. 1, and prevent movement of the arms 22 and 30 beyond the first position.

The tines 12 and 14 are angled, relative to the arms 22 and 30. This angle can range from about ninety degrees to about one hundred and thirty-five degrees. A preferred angle between the tines 12 and 14, and the arms 22 and 30, is from about one hundred degrees to about one hundred and thirty degrees. The most preferred angle range is from about one hundred and ten degrees to about one hundred and twenty degrees. The tines 12 and 14 and the arms 22 and 30 are substantially co-planar and that plane is substantially perpendicular to the axis about which the arms 22 and 30 pivot.

At least one of the tines 12 and 14 is provided with a convex surface which faces the other tine. In the embodiment shown in FIGS. 1, 1A and 11, the tine 12 includes, adjacent to its distal end 16, a convex surface 42 and it faces the tine 14. The tine 14 includes, adjacent to its distal end 24, a convex surface 44 and it faces the tine 12. The convex surfaces 42 and 44 face each other and, in a manner described hereinbelow, cooperate with each other under the controlled hand of a dentist, to shape and position matrix bands on two adjacent teeth just so in order to produce a filling in each tooth which closely approximates the shape needed to restore good contact surfaces on the adjacent teeth. Also, with the arms 22 and 30 separated, one or the other arm can be manipulated so that convex surface 42 or 44 acts on a matrix band to shape or position it.

Figure 2:
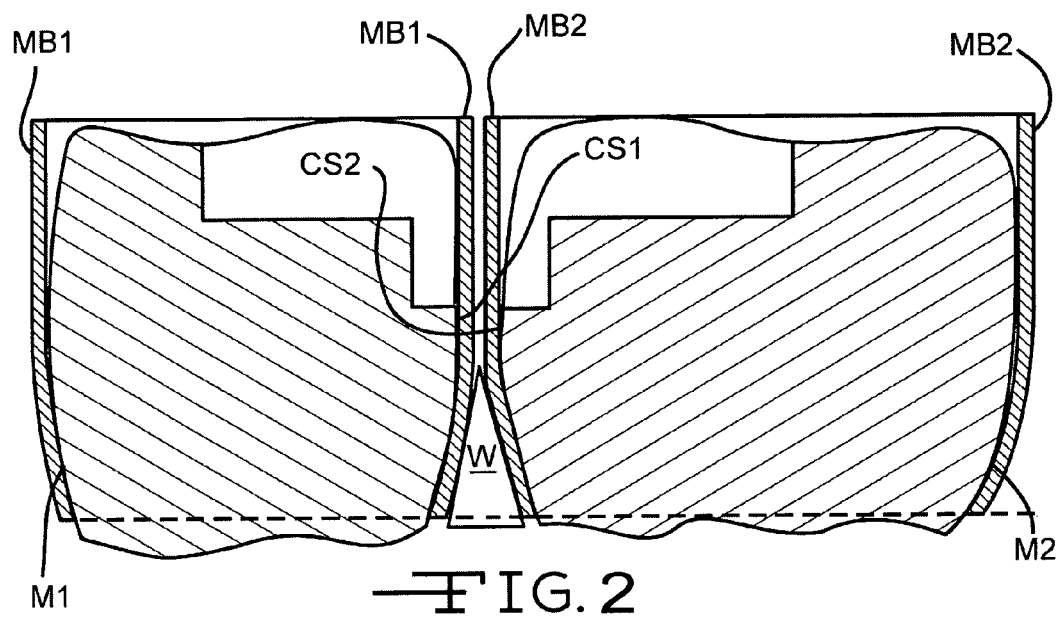
FIG. 2 is a cross-sectional view of two adjacent teeth which have been wedged apart and to which matrix bands have been applied after decayed tooth material has been excavated from the teeth.

Referring now to FIG. 2, a first molar M1 and an adjacent second molar M2 are illustrated. The molars M1 and M2 have been excavated to remove decay. A wedge W has been positioned in the embrasure between the molar M1 and the molar M2, temporarily separating the teeth and creating a space to accommodate a first matrix band MB1 in the vicinity of a contact surface CS1 of the first molar M1 and a second matrix band MB2 in the vicinity of a contact surface CS2 of the second molar M2. CS1 and CS2 face each other and, when the repair is completed, these surfaces will consist largely of surfaces of filling material. It is very important, therefore, that these surfaces mate well to seal out food and debris.

Once the matrix bands MB1 and MB2 have been positioned, as shown in FIG. 2, they must be shaped so that the filling material, when it conforms to the band shape, will form a surface having a shape closely approximating the shape of a finished contact surface, thereby minimizing the further, final shaping operation. The dental instrument 10 is suited to shaping the two bands MB1 and MB2 simultaneously while they are positioned as shown in FIGS. 2 and 3.

Figure 3:
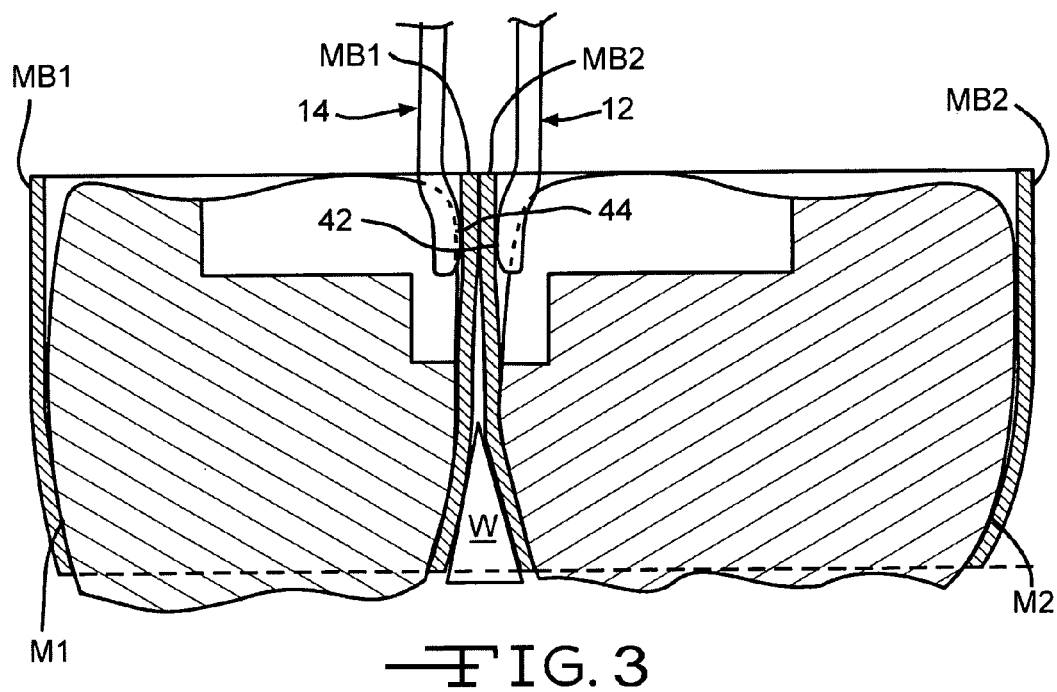
FIG. 3 is a cross sectional view of the teeth shown in FIG. 2 with tines of a dental tool according to one embodiment of the invention positioned to shape adjacent portions of the matrix bands.

The instrument 10 is manipulated to separate the distal end 16 of the tine 12 from the distal end 24 of the tine 14, as shown in FIG. 3. This separation is easily accomplished with one hand by moving the second end 36 of the first arm 22 away from the second end 40 of the second arm 30, or vice versa. The finger rings 34 and 38 may be used to advantage to manipulate the arms 22 and 30 in this manner. With the distal end 16 of the tine 12 separated from the distal end 24 of the tine 14, as shown in FIG. 3, the tines 12 and 14 are inserted into adjacent matrix bands MB2 and MB1, as shown in FIG. 3 so that the convex surface 42 is adjacent to an inside surface of the matrix band MB2 and the convex surface 44 is adjacent to an inside surface of the matrix band MB1.

Figure 4:
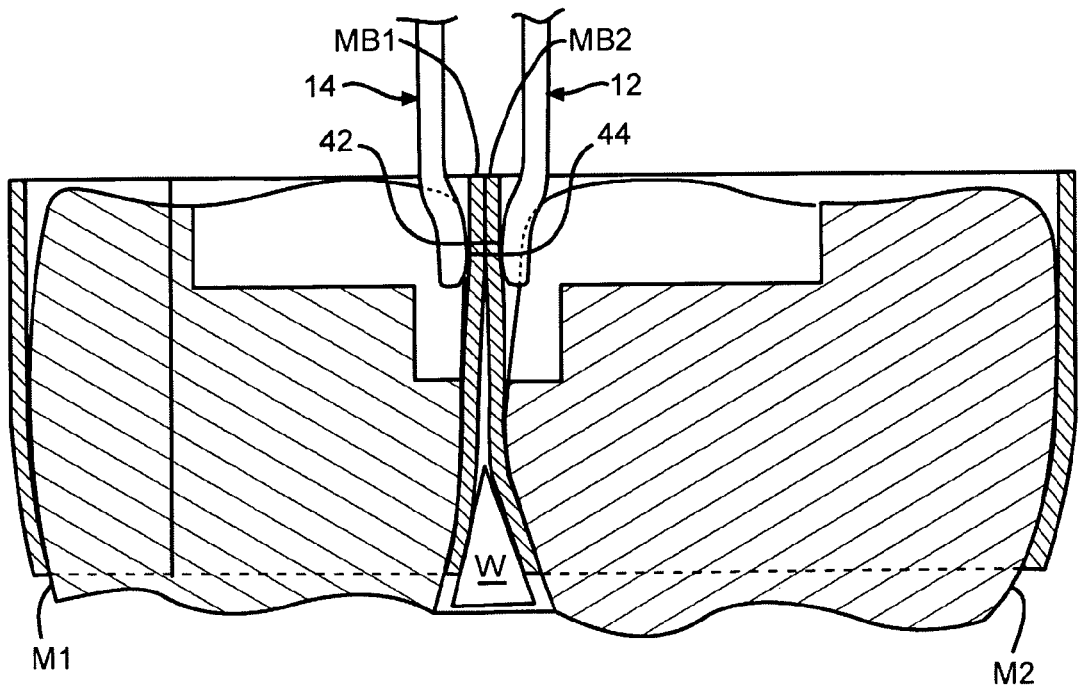
FIG. 4 is a cross sectional view of the teeth shown in the preceding two figures after some shaping of the matrix bands by the tool tines has taken place.

In order to shape the matrix bands MB 1 and MB2, the instrument 10 is manipulated to bring together the distal end 16 of the tine 12 and the distal end 24 of the tine 14, as shown in FIG. 4. This is easily accomplished with one hand by moving the second end 36 of the first arm 22 towards the second end 40 of the second arm 30, or vice versa. The finger rings 34 and 38 again may be used to advantage to manipulate the arms 22 and 30 in this manner so that the arms 22 and 30 pivot relative to each other about the pivot connection 32. This will cause the convex surface 42 to act on an inside surface of the matrix band MB2 and will cause the convex surface 44 to act on an inside surface of the matrix band MB 1, whereby these surfaces 42 and 44 will act to shape the bands in the region between the molars M1 and M2 so that the bands MB1 and MB2 will form desirable contact surfaces in the filling material. As the instrument 10 is manipulated in this manner, surface 42 acts to move a portion of said second matrix band towards the first tooth and surface 44 acts to move a portion of the first matrix band towards the second tooth. As the instrument 10 is manipulated to pivot the arms 22 and 30, the arms 22 and 30 as well as the tines 12 and 14 may remain in a substantially planar orientation.

In order to shape the matrix bands MB1 and MB2, the instrument 10 is manipulated to bring together the distal end 16 of the tine 12 and the distal end 24 of the tine 14, as shown in FIG. 4. This is easily accomplished with one hand by moving the second end 36 of the first arm 22 towards the second end 40 of the second arm 30, or vice versa. The finger rings 34 and 38 again may be used to advantage to manipulate the arms 22 and 30 in this manner so that the arms 22 and 30 pivot relative to each other about the pivot connection 32. This will cause the convex surface 42 to act on an inside surface of the matrix band MB2 and will cause the convex surface 44 to act on an inside surface of the matrix band MB1, whereby these surfaces 42 and 44 will act to shape the bands in the region between the molars M1 and M2 so that the bands MB1 and MB2 will form desirable contact surfaces in the filling material. As the instrument is manipulated to pivot the arms 22 and 30, the arms 22 and 30 as well as the tines 12 and 14 remain in a substantially planar orientation.

Figure 5:
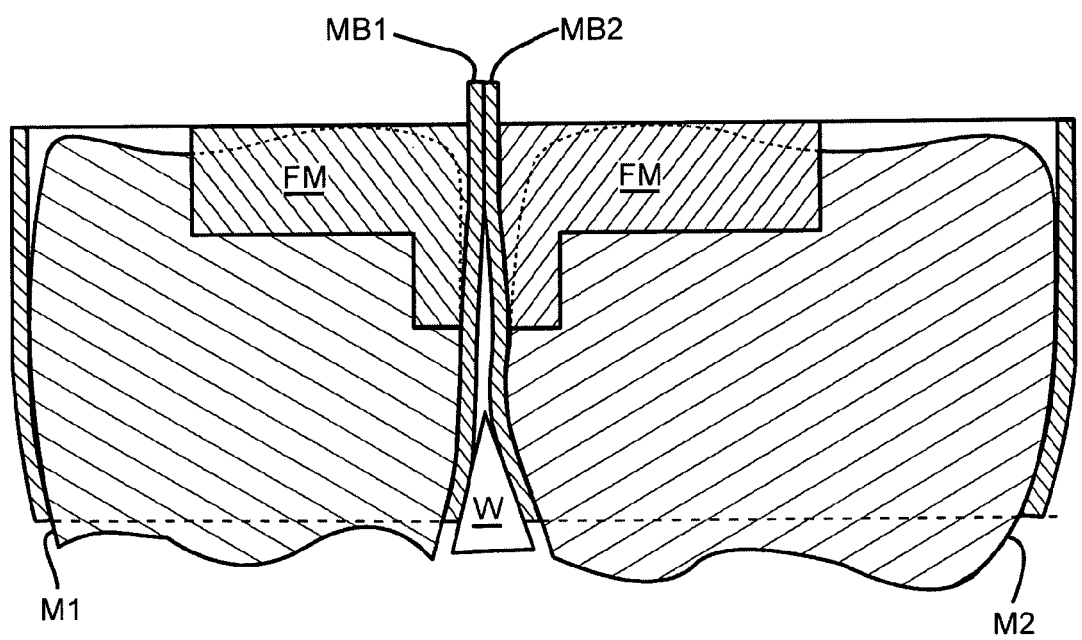
FIG. 5 is a cross sectional view of the teeth shown in the preceding three figures after filling material has been injected into the recess defined, in part, by the matrix bands around the teeth.
Figure 6:
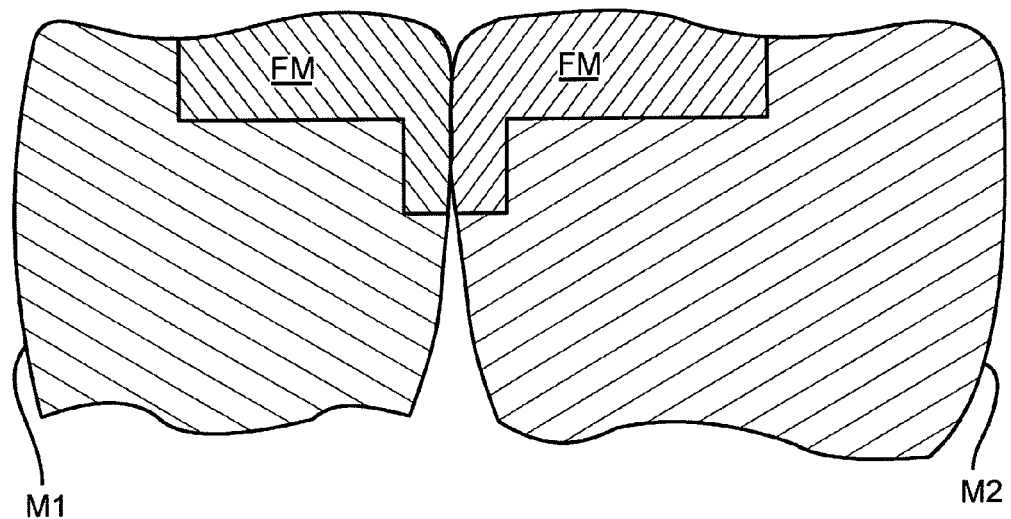
FIG. 6 is a cross sectional view of the teeth shown in the preceding four figures after the hardened filling material has been shaped.

The tines 12 and 14 are then removed from inside of the matrix bands MB1 and MB2 and filling material FM (FIG. 5) is placed into the inside of the matrix bands MB1 and MB2 where the teeth have been excavated. The filling material is then hardened or cured, and then the wedge and the bands MB1 and MB2 are removed. The restoration is then shaped by removing excess material to give the repaired teeth desirable anatomy, as shown in FIG. 6.

Thus, it can be seen that the instrument 10 greatly facilitates the simultaneous shaping of matrix bands positioned on adjacent teeth for the concurrent filling of cavities in the adjacent teeth. The convex surfaces 42 and 44 are relatively small and could be used on matrix bands applied to molars as well as pre-molars. The surfaces 42 and 44 are smaller than a desired contact surface and would be applied repeatedly in several locations of the matrix bands to impart a desired contact surface forming shape to the bands. It will be appreciated that a larger or two larger convex surfaces might be utilized to advantage. It can also be appreciated that smaller convex surfaces may be used to advantage. It will also be appreciated that different curvatures on the convex surfaces may be better suited for particular teeth. Some examples are shown in FIGS. 7 through 10.

Figure 7:
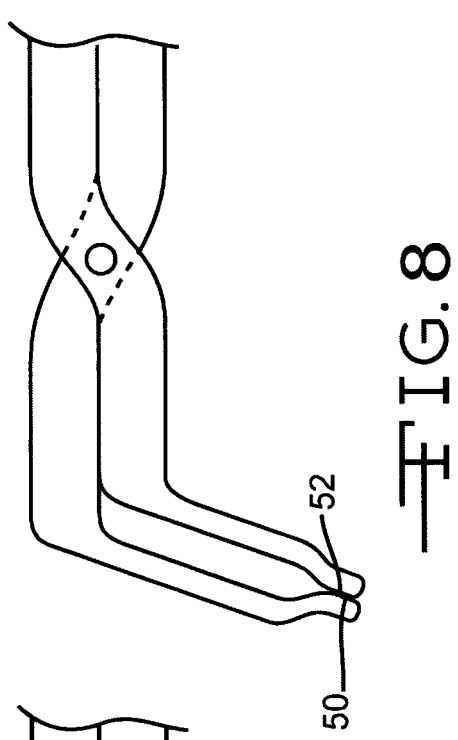
FIG. 7 is a side view showing in some detail the tine configuration of a second embodiment of a dental instrument according to the present invention.

In FIG. 7, a convex contact surface 46 is more curved and better suited to shaping a matrix band to form a contact surface in a pre-molar filling. A convex surface 48 is less curved and suited for shaping a matrix band to form a contact surface in a molar filling. The surfaces 46 and 48 are mounted on tines and they face each other.

Figure 8:
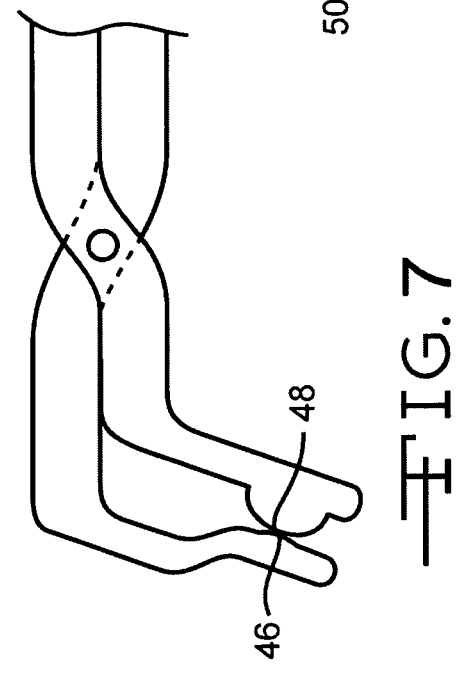
FIG. 8 is a side view showing in some detail the tine configuration of the dental instrument shown in FIGS. 1, 1A and 3 through 5.

In FIG. 8, convex surfaces 50 and 52 are the same shape and they face each other. These convex surfaces are even smaller than the surfaces 42 and 44 and they can be used in almost any instance although their smaller size will dictate that they will have to be used repeatedly on adjacent matrix bands.

Figure 9:
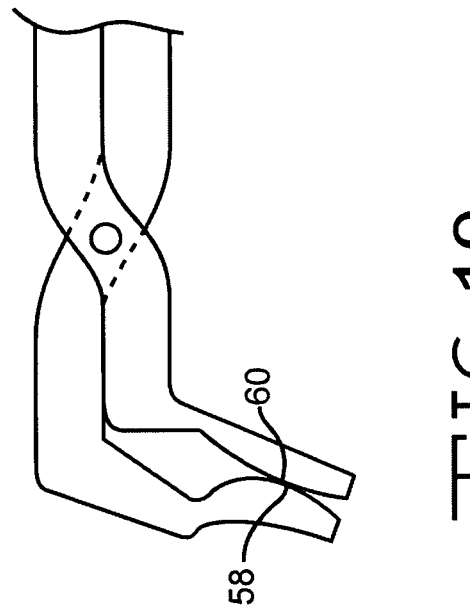
FIG. 9 is a side view showing in some detail the tine configuration of a third embodiment of a dental instrument according to the present invention.
Figure 10:
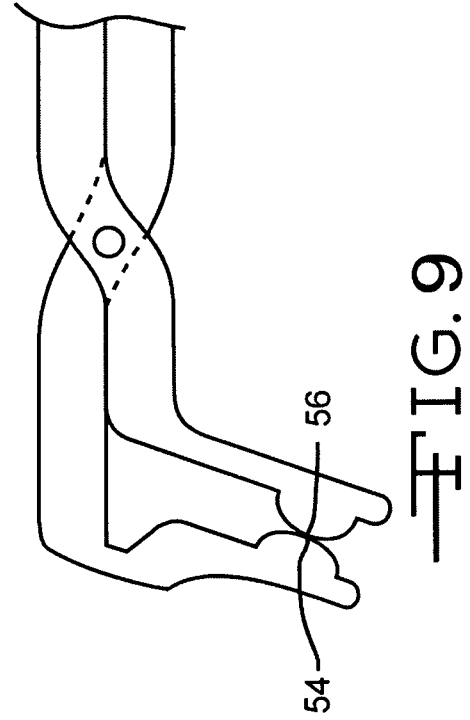
FIG. 10 is a side view showing in some detail the tine configuration of a fourth embodiment of a dental instrument according to the present invention.

In FIG. 9, convex surfaces 54 and 56 are more curved and they are the same shape. These surfaces would work well on an instrument specifically designed for use on matrix bands positioned around adjacent pre-molars. In FIG. 10, convex surfaces 58 and 60 are less curved and they are the same shape. These surfaces would work well on an instrument specifically designed for use on matrix bands positioned around adjacent molars.

Figure 12:
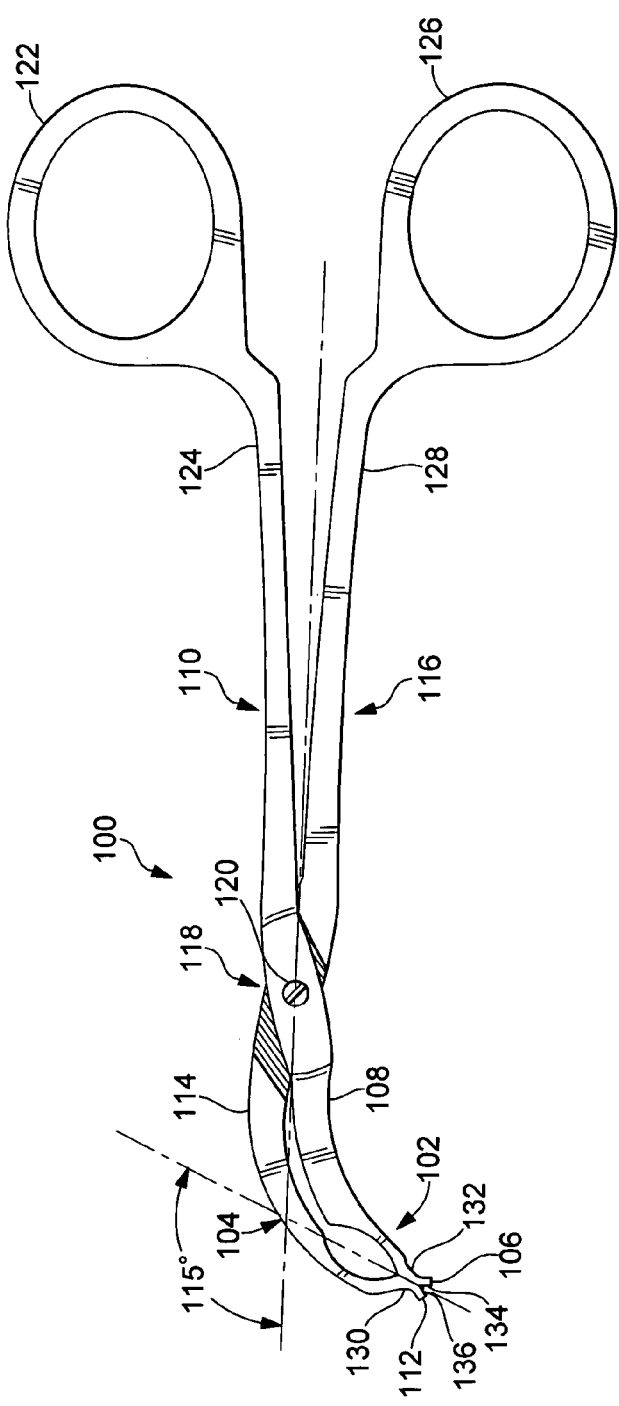
FIG. 12 is a side view of a dental instrument according to fifth embodiment of the invention.
Figure 13:
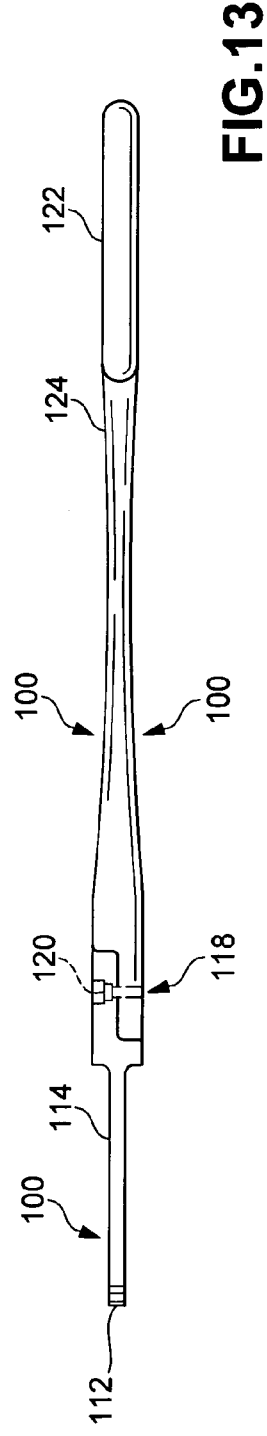
FIG. 13 is a top view of the instrument shown in FIG. 12.

Referring now in more detail to FIGS. 12 and 13, a dental instrument according to yet another embodiment of the invention is indicated generally at 100. The dental instrument comprises a first tine 102 and a second tine 104. The first tine 102 has a distal end 106 and a proximal end 108 which is supported by and depends from a first arm 110. The second tine 104 has a distal end 112 and a proximal end 114 which is supported by and depends from a second arm 116. The first arm 110 and the second arm 116 are pivotally connected at 118 by a pivot pin 120. A finger ring 122 is mounted on a distal end 124 of the first arm 110. A finger ring 126 is mounted on a distal end 128 of the second arm 116. The finger rings 122 and 126 can be manipulated towards and away from each other. When the finger rings 122 and 126 are manipulated towards each other, to the position shown in FIGS. 12 and 13, the distal ends 106 and 112 of the tines 102 and 104 are next to each other, as shown in these Figures. The distal ends 106 and 112 of the tines 102 and 104 can be separated by causing the finger rings 34 and 38 to move away from each other. This is a known scissors action and will not be described further. When the tool 100 is manipulated so that the distal ends 106 and 112 of the tines 102 and 104 engage each other, it is preferred that the distal ends 124 and 128 of the first and second arms 110 and 116 be separated a small distance as shown in FIG. 12. This way, despite some flexure in the tool, the distal ends 106 and 112 of the tines 102 and 104 can bring substantial pressure to bear on adjacent portions of two matrix bands.

The distal ends 106 and 112 of the tines 102 and 104 each have contact surfaces, 130 and 132, respectively. These contact surfaces 130 and 132 are substantial flat or planar. The distal end 106 of tine 102 is angled, relative to the contact surface 130 so that the distal end 106 extends away from the contact surface 132 of the tine 104. Similarly, the distal end 112 of tine 104 is angled, relative to the contact surface 132 so that the distal end 112 extends away from the contact surface 130 of the tine 102. When the tool 100 is manipulated to a first, closed position which is shown in FIG. 12, the distal ends 106 and 112 of the tines 102 and 104 diverge from each other. Between the contact surfaces 130 and 132 and the distal ends 106 and 112, respectively, shaping regions 134 and 136 are defined on the tines 102 and 104. The skilled hand of a dentist can manipulate the tool 100 so that the contact surfaces 130 and 132, and the shaping regions 134 and 136 act simultaneously on inside surfaces of two matrix bands positioned around adjacent teeth, thereby shaping them to have desired surface shapes. It will be appreciated that the contact surfaces 130 and 132 and the shaping regions may be configured other than as illustrated in FIG. 12.

The tines 102 and 104 are angled relative to the arms 110 and 116. This forms an included angle that can range from about ninety degrees to about one hundred and thirty-five degrees. A preferred angle between the tines 102 and 104, and the arms 110 and 116, is from about one hundred degrees to about one hundred and thirty degrees. The most preferred angle range is from about one hundred and ten degrees to about one hundred and twenty degrees. The tines 102 and 104 and the arms 110 and 116 are substantially co-planar and that plane is substantially perpendicular to the axis about which the arms 22 and 30 pivot.

It will be appreciated that considerable departures from the specific details of the embodiments of the invention described above are possible without departing from the spirit and scope of the inventions as it is defined in the following claims. For example, features of the tool 10 can be substituted, in whole or in part, into the tool 100 and vice-versa. Further, the various tool contact surfaces and shaping regions described herein can be modified, or combined into configurations having one or more features of the various disclosures, all within the scope of the invention.

I claim:

1. A method for concurrently filling cavities in a first tooth and in an adjacent second tooth, said method comprising the steps of excavating the first tooth and the second tooth to remove decay, applying a first matrix band to the first tooth to create a first recessed region, applying a second matrix band to the second tooth to create a second recessed region, separating the first tooth and the second tooth, positioning a tool comprising first and second tines extending from first and second arms that are pivotally connected to each other so that a portion of said first tine is within said first recessed region and a portion of said second tine is within said second recessed region, manipulating the tool and simultaneously shaping adjacent portions of said first and second matrix bands to move a portion of said first matrix band towards the second tooth and to move a portion of the second matrix band towards the first tooth, removing the tool, inserting filling material into the first and second recessed regions so that both recessed regions contain filling material and removing the first and second matrix bands from the first tooth and from the second tooth after both recessed regions contain filling material.

2. The method claimed in claim 1 wherein a first shaping surface is provided on said first tine, wherein a second shaping surface is provided on said second tine, and wherein, during the step of simultaneously, shaping adjacent portions of said first and second matrix bands, said first shaping surface is in contact with said first matrix band and said second shaping surface is in contact with said second matrix band.

3. The method claimed in claim 2 wherein one of said first or second shaping surfaces comprises a convex surface.

4. The method claimed in claim 1 wherein said first arm has a longitudinal axis and said first tine has a longitudinal axis and wherein said first arm longitudinal axis forms an included angle with said longitudinal axis of said first tine in the range of one hundred degrees to one hundred thirty degrees.

5. The method claimed in claim 4 wherein one of said first or second shaping surfaces comprises a convex surface.

6. A method for concurrently filling cavities in first and second teeth that are next to each other, said method comprising the steps of excavating the first and second teeth to remove decay, applying a first matrix band to the first tooth to create a first recessed region surrounded by the first matrix band, applying a second matrix band to the second tooth to create a second recessed region surrounded by the second matrix band, separating the first and second teeth, simultaneously shaping adjacent portions of said first and second matrix bands to move a portion of said first matrix band towards the second tooth and to move a portion of the second matrix band towards the first tooth with a tool comprising, a longitudinally extending first arm having first and second ends, a longitudinally extending second arm having first and second ends, a pivot connection connecting said first and second arms between their first and second ends for pivotal movement of said arms between a first position in which said second ends of said first and second arms are adjacent to each other and a second position in which said second ends of said first and second arms are spaced apart, a longitudinally extending first tine having first and second ends, said first end of said first tine being connected to said first end of said first arm so that said first tine extends laterally from said first arm, a longitudinally extending second tine having first and second ends, said first end of said second tine being connected to said first end of said second arm so that said second tine extends laterally from said second arm, a first shaping surface on said first tine, near said second end of said first tine so that said shaping surface faces, when said arms are in the first position, said second tine and a second shaping surface on said second tine, near said second end of said second tine so that said second shaping surface faces, when said arms are in the first position, said first tine, removing the tool from the matrix bands, inserting filling material into the first and second recessed regions so that both recessed regions contain filling material and removing the first and second matrix bands from the first and second teeth after both recessed regions contain filling material.

7. The method claimed in claim 6 wherein one of said first or second shaping surfaces comprises a convex surface.

8. The method claimed in claim 6 wherein said first arm has a longitudinal axis and said first tine has a longitudinal axis and wherein said first arm longitudinal axis forms an included angle with said longitudinal axis of said first tine in the range of one hundred degrees to one hundred thirty degrees.

9. The method claimed in claim 8 wherein one of said first or second shaping surfaces comprises a convex surface.

* * * * *